(12) United States Patent
Hedvati et al.

(10) Patent No.: US 7,462,737 B2
(45) Date of Patent: Dec. 9, 2008

(54) PREGABALIN FREE OF ISOBUTYLGLUTARIC ACID AND A PROCESS FOR PREPARATION THEREOF

(75) Inventors: Lilach Hedvati, Doar Na Hefer (IL); Ziv Dee-Noor, Haifa (IL); Claude Singer, Kfar Saba (IL); Gideon Pilarski, Holon (IL); Yuriy Raizi, Natanya (IL); Sharon Tomer, Tel Aviv (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 95 days.

(21) Appl. No.: 11/432,090

(22) Filed: May 10, 2006

(65) Prior Publication Data

US 2006/0276544 A1 Dec. 7, 2006

Related U.S. Application Data

(60) Provisional application No. 60/732,745, filed on Nov. 1, 2005, provisional application No. 60/731,434, filed on Oct. 27, 2005, provisional application No. 60/730,584, filed on Oct. 26, 2005, provisional application No. 60/689,699, filed on Jun. 9, 2005, provisional application No. 60/679,784, filed on May 10, 2005.

(51) Int. Cl.
C07C 205/00 (2006.01)
(52) U.S. Cl. .................................................. 562/553
(58) Field of Classification Search .................. 562/553
See application file for complete search history.

(56) References Cited

U.S. PATENT DOCUMENTS

| | | | |
|---|---|---|---|
| 5,010,189 | A | 4/1991 | Herold et al. |
| 5,599,973 | A | 2/1997 | Silverman et al. |
| 5,616,793 | A | 4/1997 | Huckabee et al. |
| 5,629,447 | A | 5/1997 | Huckabee et al. |
| 5,637,737 | A | 6/1997 | Andres et al. |
| 5,637,767 | A | 6/1997 | Grote et al. |
| 6,197,819 | B1 | 3/2001 | Silverman et al. |
| 6,333,198 | B1 | 12/2001 | Edmeades et al. |
| 6,488,964 | B2 | 12/2002 | Bruna et al. |
| 6,891,059 | B2 | 5/2005 | Burk et al. |
| 6,924,377 | B2 | 8/2005 | Blazecka et al. |
| 7,141,695 | B2 | 11/2006 | Przewosny et al. |
| 2001/0016665 | A1 | 8/2001 | Grote et al. |
| 2003/0225149 | A1 | 12/2003 | Blazecka et al. |
| 2005/0222464 | A1 | 10/2005 | Hoge, II |
| 2005/0228190 | A1 | 10/2005 | Bao et al. |
| 2005/0283023 | A1 | 12/2005 | Hu et al. |
| 2006/0270871 | A1 | 11/2006 | Khanduri et al. |
| 2007/0073085 | A1 | 3/2007 | Hedvati et al. |
| 2008/0014280 | A1 | 1/2008 | Kumar et al. |

FOREIGN PATENT DOCUMENTS

| | | |
|---|---|---|
| CN | 1 634 869 | 7/2005 |
| CZ | 297 970 | 3/2007 |
| WO | WO 96/38405 A1 | 12/1996 |
| WO | WO 96/40617 A1 | 12/1996 |
| WO | WO 01/55090 A1 | 8/2001 |
| WO | WO 2006/000904 A2 | 1/2005 |
| WO | WO 2005/100580 | 10/2005 |
| WO | WO 2006/008640 | 1/2006 |
| WO | WO 2006/136087 | 12/2006 |
| WO | WO 2008/004044 | 1/2008 |
| WO | WO 2008/007145 | 1/2008 |
| WO | WO 2008/009897 | 1/2008 |

OTHER PUBLICATIONS

Hoekstra et al. "Chemical Development of CI-1008, An Enantiomerically Pure Anticonvulsant", *Organic Process Research And Development*, vol. 1, No. 1, pp. 26-38, (1997).
Martin et al. "Pregabalin: CI-1008, PD-144723" *Drugs of the Future*, vol. 24, No. 8, pp. 862-870, (1999).
Strobel et al., *Chemical Instrumentation: A Systematic Approach*, 3rd Ed., (1989), pp. 391-393, 879-894, 922-925, 953.
Andruszkiewicz and Silverman, "A Convenient Synthesis of 3-Alkyl-4-Aminobutanoic Acids", *Synthesis*, 953-955 (1989).
Barnes et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", *J. Am.Chem.Soc.* 124(44): 13097-13105 (2002).
Berner et al., "Asymmetric Michael Additions to Nitroalkenes", *European Journal of Organic Chemistry*, 1877-1894 (2002).
Cason et al., "Branched-Chain Fatty Acids. XXVII. Further Study of the Dependence of Rate to Amide Hydrolysis on Substitution near the Amide Group. Relative Rates of Hydrolysis of Nitrile to Amide and Amide to Acid", *J. Org. Chem.*, 18,(9):1129-1136 (1953).
Chen et al., "Synthesis of Pregabalin", *Zhongguo YiYao Gongye Zazhi*, 35(4):195-196 (2004).
Colonge et al. : "Preparation De Pyrrolidones-2 et de Gamma-Aminoacides", *Bulletin De La Societe Chimique De France, Societe Francaise De Chimie*, 598-603 (1962).
Day and Thorpe, "The Formation and Reactions of Imino-compounds. Part XX. The Condensation of Aldehydes with Cyanoacetamide", *J. Chem. Soc.*, 117: 1465-1474 (1920).
Karanewsky et al., "Practical Synthesis of an Enantiomerically Pure Synthon for the Preparation of Mevinic Acid Analogues", *J. Org. Chem.* 56(11): 3744-3747 (1991).
Li et al., "Highly Enantioselective Catalytic Conjugate Addition of Malonate and β-Ketoester to Nitroalkenes: Asymmetric C-C Bond Formation with New Bifunctional Organic Catalysts Based on Cinchona Alkaloids", *J. Am. Chem. Soc.*, 126(32): 9906-9907 (2004).
Okino et al., "Entantio- and Diastereoselective Michael Reaction of 1,3-Dicarbonyl Compounds to Nitroolefins Catalyzed by a Bifunctional Thiourea", *J. Am.Chem.Soc.*, 127(1): 119-125 (2005).

(Continued)

*Primary Examiner*—Jafar Parsa
(74) *Attorney, Agent, or Firm*—Kenyon & Kenyon LLP

(57) ABSTRACT

A Pregabalin having a low level of 3-isobutylglutaric acid is provided.

6 Claims, No Drawings

OTHER PUBLICATIONS

Sammis et al., "Highly Enantioselective Catalytic Conjugate Addition of Cyanide to α,β-Unsaturated Imides", *J. Am. Chem. Soc.*, 125(15): 4442-4443 (2003).

Shintani et al., "Highly Enantioselective Desymmetrization of Anhydrides by Carbon Nucleophiles: Reactions of Grignard Reagents in the presence of (−)-Sparteine", *Angewandte Chemie, International Edition*, 41(6):1057-1059 (2002).

Snyder et al., Introduction To Modern Liquid Chromatography, 549-572, 2nd Ed., John Wiley & Sons, Inc. (1979).

Theisen et al., "Prochiral Recognition in the Reaction of 3-Substituted Glutaric Anhydrides with Chiral Secondary Alcohols", *J. Org. Chem.*, 58(1):142-146 (1993).

Verma et al., "Desymmetrization of prochiral anhydrides with Evans' oxazolidinones: an efficient route to homochiral glutaric and adipic acid derivatives", *Journal of the Chemical Society, Perkin Transactions 1: Organic and Bio-Organic Chemistry*, 257-264 (1999).

Yamamoto et al., "Stereoselective Synthesis of (E)-Alkylidenesuccinates by Palladium-catalyzed Carbonylation", *Bull.Chem.Soc.Japan*, 58(11): 3397-3398 (1985).

PREGABALIN FREE OF ISOBUTYLGLUTARIC ACID AND A PROCESS FOR PREPARATION THEREOF

RELATED APPLICATIONS

This application claims the benefit of U.S. Provisional Application Nos. 60/679,784, filed May 10, 2005, 60/689,699, filed Jun. 9, 2005, 60/730,584, filed Oct. 26, 2005, 60/731,434, filed Oct. 27, 2005, and 60/732,745, filed Nov. 1, 2005, the contents of which are incorporated herein in their entirety.

FIELD OF INVENTION

The present invention relates to Pregabalin having a low level of 3-isobutylglutaric acid, and processes for preparing Pregabalin having a low level of 3-isobutylglutaric acid.

BACKGROUND OF THE INVENTION (S)-Pregabalin, (S)-(+)-3-(aminomethyl)-5-methylhexanoic acid, a compound having the chemical structure,

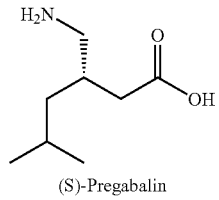

(S)-Pregabalin is a γ-amino butyric acid or (S)-3-isobutyl (GABA) analogue. (S)-Pregabalin has been found to activate GAD (L-glutamic acid decarboxylase). (S)-Pregabalin has a dose dependent protective effect on-seizure, and is a CNS-active compound. (S)-Pregabalin is useful in anticonvulsant therapy, due to its activation of GAD, promoting the production of GABA, one of the brain's major inhibitory neurotransmitters, which is released at 30 percent of the brains synapses.

(S)-Pregabalin has analgesic, anticonvulsant, and anxiolytic activity. (S)-Pregabalin is marketed under the name LYRICA® by Pfizer, Inc., in tablets of 25, 50, 75, 150, 200, and 300 mg doses.

The preparation of (S)-Pregabalin from 3-isbutylglutaric acid is disclosed in DRUGS OF THE FURTURE, 24 (8), 862-870 (1999), and in U.S. Pat. No. 5,616,793, and is described by the following Scheme:

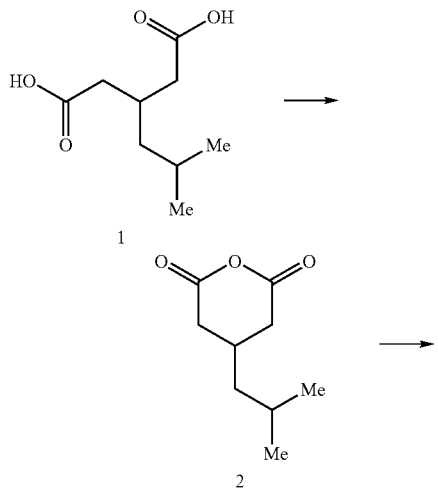

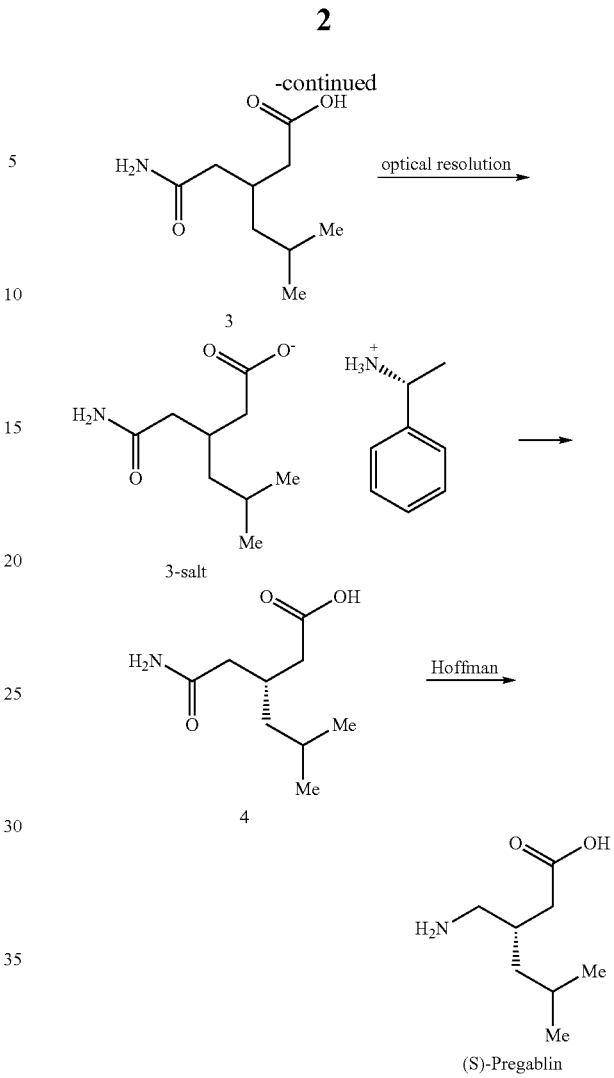

Accordingly, 3-isobutylglutaric acid, compound 1, is converted into the corresponding anhydride, compound 2, by treatment with acetic anhydride. The reaction of the anhydride with $NH_4OH$ produces the glutaric acid mono-amide, compound 3, which is resolved with (R)-1-phenylethylamine, yielding the (R)-phenylethylamine salt of (R)-3-(carbamoylmethyl)-5-methylhexanoic acid, compound 3-salt. Combining the salt with an acid liberates the R enantiomer, compound 4. Finally, Hoffmann degradation with $Br_2$/NaOH provides (S)-Pregabalin.

In the above processes, the compound 3-isobutylglutaric acid (referred to as CMH-diacid), having the following structure:

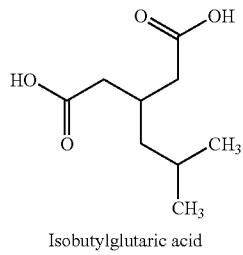

Isobutylglutaric acid is used as a precursor for 3-carbamoylmethyl-5-methyl hexanoic acid-racemate (referred to as CMH-racemate) of formula 3, which leads to (S)-Pregabalin.

Impurities in (S)-Pregabalin, such as, CMH-diacid and others, or in any active pharmaceutical ingredient (API) are undesirable and, in extreme cases, might even be harmful to a patient being treated with a dosage form containing the API.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as (S)-Pregabalin, it must be analyzed for purity, typically, by HPLC or TLC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. As discussed above, in the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a chromatogram, or a spot on a TLC plate. (Strobel p. 953, Strobel, H.A.; Heineman, W. R., Chemical Instrumentation: A Systematic Approach, 3rd ed. (Wiley & Sons: New York 1989)). Thereafter, the impurity can be identified, e.g., by its relative position in the chromatogram, where the position in a chromatogram is conventionally measured in minutes between injection of the sample on the column and elution of the particular component through the detector. The relative position in the chromatogram is known as the "retention time."

As is known by those skilled in the art, the management of process impurities is greatly enhanced by understanding their chemical structures and synthetic pathways, and by identifying the parameters that influence the amount of impurities in the final product.

Thus, there is a need in the art for Pregabalin and (S)-Pregabalin having a low level of CMH-diacid and for a process for preparation thereof.

SUMMARY OF THE INVENTION

In one aspect, the present invention provides Pregabalin containing about 0.15% to the detection limit of an HPLC method of CMH-diacid, of the following structure.

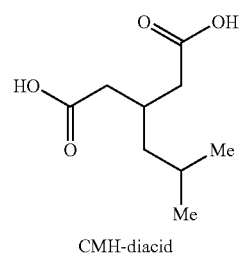

CMH-diacid

In another aspect, the present invention provides Pregabalin containing about 0.10% to the detection limit of an HPLC method of CMH-diacid.

In yet another aspect, the present invention provides Pregabalin containing about 0.07% to the detection limit of an HPLC method of CMH-diacid.

In one aspect the present invention provides pharmaceutical formulation comprising (S)-Pregabalin containing about 0.15% to the detection limit of an HPLC method of CMH-diacid and pharmaceutically acceptable excipients.

In another embodiment, the present invention provides a process for preparing pharmaceutical formulation comprising mixing (S)-Pregabalin containing about 0.15% to the detection limit of an HPLC method of CMH-diacid and a pharmaceutically acceptable carrier.

In yet another embodiment, the present invention provides the use of (S)-Pregabalin containing about 0.15% to the detection limit of an HPLC method of CMH-diacid for the manufacture of a pharmaceutical composition.

DETAILED DESCRIPTION OF THE INVENTION

As used herein, unless specified otherwise, the term "CMH" refers to either the R enantiomer of CMH ((R)-CMH) or to the CMH racemate.

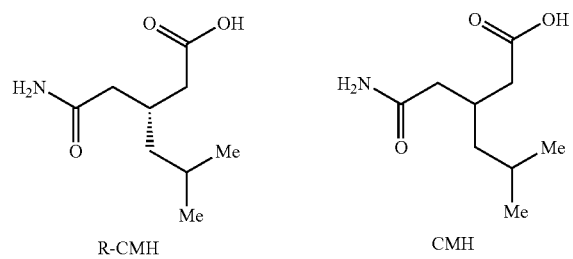

R-CMH                           CMH

As used herein, unless specified otherwise, the term "Pregabalin" refers to either the S enantiomer of Pregabalin ((S)-Pregabalin) or to the Pregabalin racemate.

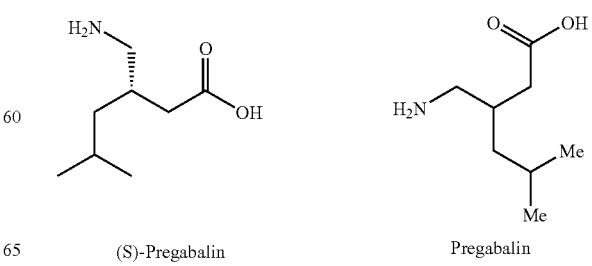

(S)-Pregabalin                  Pregabalin

As used herein, unless specified otherwise, when CMH racemate is used, Pregabalin racemate is obtained.

As used herein, unless specified otherwise, when (R)-CMH is used, (S)-Pregabalin is obtained.

The present invention provides Pregabalin containing about 0.15% to the detection limit of an HPLC method of CMH-diacid of the following structure.

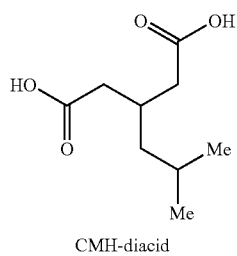

CMH-diacid

Preferably, the Pregabalin of the present invention contains about 0.15% to about 0.03% area by HPLC of CMH-diacid.

The present invention further provides Pregabalin containing about 0.10% to the detection limit of an HPLC method of CMH-diacid Preferably, the Pregabalin of the present invention contains about 0.10% to about 0.03% area by HPLC of CMH-diacid.

The present invention also provides Pregabalin containing about 0.07% to the detection limit of an HPLC method of CMH-diacid Preferably, the Pregabalin of the present invention contains about 0.07% to about 0.03% area by HPLC of CMH-diacid.

The detection limit of an HPLC method refers to any HPLC method used to determine the purity of Pregabalin, and in particular, to determine the amount of CMH-diacid in Pregabalin. Preferably, the detection limit is the detection limit of the HPLC method used in the present invention or of any other equivalent method.

The CMH used to prepare Pregabalin does not contain CMH-diacid from earlier stages of the synthesis; however, when converted to Pregabalin, CMH undergoes hydrolysis, to give the impurity CMH-diacid. CMH-diacid, which is a major impurity in Pregabalin, is very difficult to remove. Therefore, method for controlling its formation, and methods for its purification are advantageous. The present invention includes a method for controlling the level of CMH-diacid by maintaining at low temperatures the aqueous solution of the alkali hydroxide when combining with R-CMH, and when adding bromine, in a drop-wise manner. Hence, controlling the temperature during the additions, allows controlling the amount of CMH-diacid formed during the reaction. The process also includes purifying Pregabalin by selective extractions of the acidic salt of Pregabalin by the utilization of carefully chosen solvents and/or mixtures of solvents, followed by crystallization, and, thus, providing substantially pure Pregabalin.

The method for controlling the level of CMH-diacid in Pregabalin includes combining water and an an alkali hydroxide selected from a group consisting of sodium hydroxide, potassium hydroxide, lithium hydroxide and cesium hydroxide; adding CMH at a temperature of about 0° C. to about 20° C., and adding bromine, in a drop-wise manner, at a temperature of about 0° C. to about 25° C. The addition of CMH to the aqueous basic solution and the reaction of bromine with the mixture of CMH, water, and the alkali base are exothermic. Hence, controlling the temperature during the additions, by a drop-wise addition of bromine and by constant cooling, facilitates the regulation of the amount of CMH-diacid, formed by hydrolysis of CMH under basic conditions.

Pregabalin containing about 0.15% to the detection limit of an HPLC method of CMH-diacid can be prepared by combining water and an alkali hydroxide; adding CMH at a temperature of about 0° C. to about 20° C.; adding bromine, in a drop-wise manner, at a temperature of about 0° C. to about 25° C.; heating to a temperature of about 40° C. to about 100° C.; reacting with a strong mineral acid; extracting with a $C_{4-8}$ alcohol; mixing with a base, and crystallizing from a $C_{4-8}$ alcohol.

Pregabalin containing about 0.07% to the detection limit of an HPLC method of CMH-diacid can be prepared by combining water and an alkali hydroxide selected from a group consisting of sodium hydroxide, potassium hydroxide, lithium, hydroxide and cesium hydroxide; adding CMH at a temperature of about 5° C. to about 10° C.; adding bromine, in a drop-wise manner, at a temperature of about 5° C. to about 10° C.; heating to a temperature of about 40° C. to about 100° C.; reacting with a strong mineral acid selected from a group consisting of $H_2SO_4$, HCl, HBr and $H_3PO_4$; extracting with a $C_{4-8}$ alcohol selected from a group consisting of butanol, iso-butanol, 2-butanol, pentanol or iso-pentanol; mixing with a base selected from a group consisting of diisopropylamine, dipropylamine, tributyl amine, triethyl amine, sodium hydroxide, potassium hydroxide, cesium hydroxide, sodium carbonate, sodium bicarbonate and potassium carbonate, and crystallizing from a $C_{4-8}$ alcohol selected from a group consisting of butanol, iso-butanol, 2-butanol, pentanol or iso-pentanol.

The preparation of Pregabalin, as described above, may be illustrated by the following scheme:

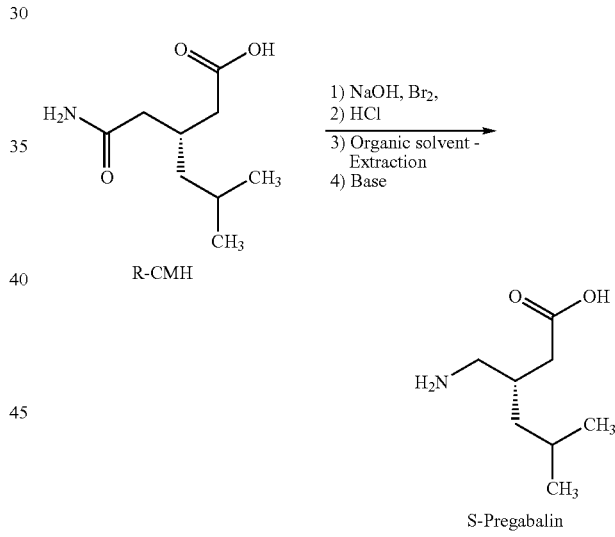

CMH may be obtained, for example, according to the process disclosed in U.S. Pat. No. 5,616,793.

Pregabalin obtained by the processes of the present invention contains CMH-diacid. The obtained Pregabalin may contain CMH-diacid between 0.15% to about the detection limit of an HPLC method, preferably, between about 0.15% to about 0.03% area by HPLC, or between 0.10% to the detection limit of an HPLC method, preferably, between about 0.10% to about 0.03% are by HPLC, or between 0.07% to the detection limit of an HPLC method, preferably, between about 0.07% to about 0.03% are by HPLC.

Preferably, the alkalai hydroxide is sodium hydroxide. Preferably, the alkali hydroxide is used in a form of an aqueous solution.

Typically, the mixture obtained after combining CMH and the alkalai hydroxide has a pH of at least about 13, preferably at least about 14.

Preferably, the bromine is added in an amount of 1 mole equivalents to about 1.4 mole equivalents per mole equivalents of CMH. Preferably, the drop-wise addition is done over a period of about 12 minutes to about 180 minutes, more preferably, of about 30 to about 45 minutes.

Preferably, heating is done to a temperature of about 60° C. to about 85° C. Preferably, heating is done for about 15 minutes to about 4 hours, more preferably, for about 15 minutes to about an hour, prior to the addition of the strong mineral acid.

Preferably, cooling to a temperature of about 40° C. to about 20° C. is done, prior to the addition of the strong mineral acid. Preferably, the strong mineral acid is $H_2SO_4$.

Preferably, when adding the strong mineral acid, a salt of Pregabalin with the strong mineral acid may be obtained. This salt is separated from CMH-diacid by selective extractions with $C_{4-8}$ alcohol. The extractions are selective due to the difference in the solubility of the salt in water vs. the solubility of CMH-diacid in water. The preferred $C_{4-8}$ alcohol is iso-butanol.

Preferably, the organic phase obtained from the extraction process is combined with a base, to obtain a precipitate of Pregabalin. Preferably, the base is either an organic base or an inorganic base. The preferred organic base is either a secondary or tertiary amine. Preferably, the secondary amine is either diisopropylamine or dipropylamine. A preferred tertiary amine is tributyl amine or triethyl amine. More preferably, the organic base is tributyl amine. Preferably, the inorganic base is an alkali hydroxide or an alkali carbonate. A preferred alkali hydroxide is sodium hydroxide, potassium hydroxide, lithium hydroxide, or cesium hydroxide. A preferred alkali carbonate is sodium carbonate, sodium bicarbonate, or potassium carbonate. The more preferred base is an organic base, most preferably, a tertiary amine, and even most preferably, tributylamine.

Preferably, Pregabalin may be crystallized by heating the obtained precipitate to a temperature of about 50° C. to about 110° C., more preferably, to about 60° C. to about 110° C., most preferably, to about 90° C. to about 110° C., to obtain a solution, and cooling to a temperature of less than about 25° C., preferably, to a temperature of about 25° C. to about −10° C., more preferably, to about 10° C. to about 2° C., to obtain a precipitate of Pregabalin, wherein, the CMH-diacid remains soluble in the solution. The precipitate of Pregabalin may be isolated by filtering off, washing, and drying in a vacuum oven.

The Pregabalin used as starting material in the crystallization process may contain at least about 0.15% area by HPLC of CMH-diacid. Also usable is Pregabalin containing at least about 0.10% area by HPLC of CMH-diacid, and also usable is Pregabalin containing at least about 0.07% area by HPLC of CMH-diacid.

Determining the level of CMH-diacid in Pregabalin may be done by using an HPLC method comprising combining a Pregabalin sample with a mixture of acetonitrile:methanol:buffer in a ratio of about 1:1:8, to obtain a solution; injecting the solution into a 250×4.6 mm Inertsil ODS 3V (or similar) column, followed by eluting the sample from the column at about 50 min using a mixture of acetonitrile:methanol:buffer (1:1:8) (referred to as eluent A) and acetonitrile (referred to as eluent B) as an eluent, and measuring the CMH-diacid content in the relevant sample with a UV detector (preferably, at 210 nm).

The present invention also provides pharmaceutical formulation comprising (S)-Pregabalin containing about 0.15% to the detection limit of an HPLC method of CMH-diacid and pharmaceutically acceptable excipients.

The present invention provides a process for preparing pharmaceutical formulation comprising mixing (S)-Pregabalin containing about 0.15% to the detection limit of an HPLC method of CMH-diacid and a pharmaceutically acceptable carrier.

The present invention further provides the use of (S)-Pregabalin containing about 0.15% to the detection limit of an HPLC method of CMH-diacid for the manufacture of a pharmaceutical composition.

As used herein, the term "pharmaceutical compositions" includes tablets, pills, powders, liquids, suspensions, emulsions, granules, capsules, suppositories, or injection preparations. The pharmaceutical composition is preferably formulated without the use of acidic excipients. Pharmaceutical compositions containing the Pregabalin of the present invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

Any excipient commonly known and used widely in the art can be used in the pharmaceutical composition. Carriers used include, but are not limited to, lactose, white sugar, sodium chloride, glucose, urea, starch, calcium carbonate, kaolin, crystalline cellulose, silicic acid, and the like. Binders used include, but are not limited to, water, ethanol, propanol, simple syrup, glucose solutions, starch solutions, gelatin solutions, carboxymethyl cellulose, shellac, methyl cellulose, potassium phosphate, polyvinylpyrrolidone, and the like. Disintegrating agents used include, but are not limited to, dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, and the like. Disintegration inhibitors used include, but are not limited to, white sugar, stearin, coconut butter, hydrogenated oils, and the like. Absorption accelerators used include, but are not limited to, quaternary ammonium base, sodium laurylsulfate, and the like. Wetting agents used include, but are not limited to, glycerin, starch, and the like. Adsorbing agents used include, but are not limited to, starch, lactose, kaolin, bentonite, colloidal silicic acid, and the like. Lubricants used include, but are not limited to, purified talc, stearates, boric acid powder, polyethylene glycol, and the like. Tablets can be further coated with commonly known coating materials such as sugar coated tablets, gelatin film coated tablets, tablets coated with enteric coatings, tablets coated with films, double layered tablets, and multi-layered tablets.

When shaping the pharmaceutical composition into pill form, any commonly known excipient used in the art can be used. For example, carriers include, but are not limited to, lactose, starch, coconut butter, hardened vegetable oils, kaolin, talc, and the like. Binders used include, but are not limited to, gum arabic powder, tragacanth gum powder, gelatin, ethanol, and the like. Disintegrating agents used include, but are not limited to, agar, laminalia, and the like.

For the purpose of shaping the pharmaceutical composition in the form of suppositories, any commonly known excipient used in the art can be used. For example, excipients include, but are not limited to, polyethylene glycols, coconut butter, higher alcohols, and esters of higher alcohols, gelatin, and semisynthesized glycerides.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic.

Additional ingredients, such as dissolving agents, buffer agents, and analgesic agents may be added. If necessary, coloring agents, preservatives, perfumes, seasoning agents, sweetening agents, and other medicines may also be added to the desired preparations.

The amount of Pregabalin contained in a pharmaceutical composition for treating schizophrenia should be sufficient to treat, ameliorate, or reduce the symptoms associated with schizophrenia. Preferably, Pregabalin is present in an amount of about 1% to about 70% by weight, and more preferably from about 1% to about 30% by weight of the dose.

The pharmaceutical compositions of the invention may be administered in a variety of methods depending on the age, sex, and symptoms of the patient. For example, tablets, pills, solutions, suspensions, emulsions, granules, and capsules may be orally administered. Injection preparations may be administered individually or mixed with injection transfusions such as glucose solutions and amino acid solutions intravenously. If necessary, the injection preparations may be administered intramuscularly, intracutaneously, subcutaneously or intraperitoneally. Suppositories may be administered into the rectum.

The dosage of a pharmaceutical composition for treating schizophrenia according to the invention will depend on the method of use, the age, sex, and condition of the patient. Preferably, Pregabalin is administered in an amount from about 0.1 mg/kg to about 10 mg/kg of body weight/day. More preferably, about 1 mg to 200 mg of Pregabalin may be contained in a dose.

The invention also encompasses methods of making a pharmaceutical formulation comprising combining Pregabalin, and a pharmaceutically acceptable excipient. As used herein, the term "pharmaceutical formulations" includes tablets, pills, powders, liquids, suspensions, solutions, emulsions, granules, capsules, suppositories, or injection preparations.

Having described the invention with reference to certain preferred embodiments, other embodiments will become apparent to one skilled in the art from consideration of the specification. The invention is further defined by reference to the following examples describing in detail the preparation of the compound of the present invention. It will be apparent to those skilled in the art that many modifications, both to materials and methods, may be practiced without departing from the scope of the invention.

EXAMPLES

The analysis for Isobutylglutaric acid (CMH-Diacid) is done in Pregabalin crude, by the following method:

| HPLC | Inertsil ODS 3 V, 250 * 4.6 mm, 5µ. C.N 5020-01802 |
|---|---|
| Eluent A: | 80% 0.04M $(NH_4)_2HPO_4$ adjusted to pH = 6.5 with $H_3PO_4$ 10% Acetonitrile 10% Methanol |
| Eluent B: | Acetonitrile |
| Stop time: | 50 min |
| Gradient of Eluent: | Time (min) Eluent A (%) Eluent B (%) |
| | 0    100    0 |
| | 6    100    0 |
| | 50    65    35 |

-continued

| Equilibration time: | 10 min |
|---|---|
| Flow: | 0.8 ml/min |
| Detector: | 210 nm |
| Injection volume: | 20 µL |
| Diluent: | Eluent A |
| Column temperature: | 25° C. |
| Autosampler temperature: | 5° C. |

Quantification limit of the method is 0.03%.
The detection limit may be lower than 0.03% as the peak of CMH-diacid can be detected in the chromatogram.

Example 1

Preparation of (S)-Pregabalin

A reactor (0.2 l) was loaded with water (150 ml) and NaOH (32.3 gr) to obtain a solution. The solution was cooled to 5° C. and (R)-CMH (30 gr) was added. $Br_2$ (25.9 g) was then added dropwise (15 min) while keeping the temperature below 10° C. The mixture was heated to 60° C. for 15 minutes, and then cooled to room temperature. Iso-butanol was added (90 ml), followed by a solution of $H_2SO_4$ (66%) (32 ml). The phases were separated, and the aqueous phase was extracted with Iso-butanol (75 ml). $Bu_3N$ (32.6 ml) was added to the combined organic phases. The mixture was heated to dissolution, and then was cooled to 2° C., and stirred for 1.5 hour. The solid was filtered, washed, and dried at 55° C. under vacuum, providing an 80.4% yield. Total purity: 99.7% area by HPLC, CMH-Diacid—less than 0.03% area by HPLC.

Example 2

Preparation of Pregabalin

A reactor (1 l) was loaded with water (200 ml) and NaOH (34.7 g). The solution was cooled to 5° C. and R-CMH (40 g) was added. $Br_2$ (34.7 g) was added drop-wise (15 min) while keeping the temperature below 10° C. The mixture was heated to 60° C. for 15 minutes and then cooled to RT. Iso-butanol (120 ml) and then a solution of $H_2SO_4$—66% (40 ml) was added (pH=3). The mixture was heated to 33° C., then the phases were separated, and the aqueous phase was extracted with Iso-butanol (100 ml). The combined organic phases was cooled to 2° C. for 2.5 hours, and filtered to remove inorganic salts. The filtrate was heated to RT, and $Bu_3N$ (41.6 g) was added to the organic phase. The mixture was heated to dissolution and then was cooled to 2° C., and stirred for 2 hours. The solid was filtered and the cake washed with i-BuOH (40 ml). Calculated yield of 79.4%. CMH-Diacid—0.07% area by HPLC.

Example 3

Preparation of (S)-Pregabalin

A reactor (0.5 l) was loaded with water (175 ml) and NaOH (37.6 g) to obtain a solution. The solution was cooled to 10° C., and (R)-CMH (35 g) was added. $Br_2$ (30.24 g) was added dropwise during a period of 0.5 hour, while keeping the temperature below 25° C. The mixture was heated to 60° C. for 15 minutes, and then cooled to room temperature. The solution was separated to 2 portions.

Half of the first portion (equal to 5 g of (R)-CMH) was stirred for 5 hours at room temperature, then Iso-butanol (15 ml) and a solution of $H_2SO_4$ (66%) (5 ml) were added. The phases were separated, and the aqueous phase was extracted with Iso-butanol (12 ml). $Bu_3N$ (5.2 g) was added to the comined organic phases. The solution was cooled to 2° C., and stirred for 1.5 hours. The solid was filtered, washed and dried at 55° C. under vacuum, providing (S)-PREGABALIN with a total purity of 99.3% area by HPLC, CMH-Diacid—0.09% area by HPLC.

The second portion was treated as follows:

Iso-butanol was added (75 ml), and then a solution of $H_2SO_4$ (66%) (25 ml) was added. The phases were separated, and the aqueous phase was extracted with Iso-butanol (62 ml). The solution was separeted again to 2 portions (portions A & B).

An amount of portion A (equal to 5 g of (R)-CMH) was stirred for 24 hours at room temperature, $Bu_3N$ (2.6 gr) was added, and the solution was cooled to 2° C., and stirred for 1.5 hours. The solid was filtered, washed and dried at 55° C. under vacuum, providing (S)-PREGABALIN with total purity of 99.07% area by HPLC, CMH-Diacid—0.03% area by HPLC.

An amount of portion A (equal to 5 g of (R)-CMH) was stirred for 0.5 hour at room temperature, $Bu_3N$ (2.6 gr) was added, and the solution was cooled to room temperature, and stirred for 24 hours. The solid was filtered, washed, and dried at 55° C. under vacuum, providing (S)-PREGABALIN with a total purity of 99.67% area by HPLC, CMH-Diacid—less than 0.03% area by HPLC.

Example 4

Preparation of (S)-Pregabalin

A reactor (0.2 l) was loaded with water (150 ml) and NaOH (32.3 g) to obtain a solution. The solution was cooled to 15° C., and (R)-CMH (30 g) was added. $Br_2$ (25.9 g) was added dropwise (15 min) while keeping the temperature below 20° C. The mixture was heated to 60° C. for 15 minutes, and then cooled to room temperature. Iso-butanol was added (150 ml), and then a solution of $H_2SO_4$ (66%) (30 ml) was added. The phases were separated, and the aqueous phase was extracted with Iso-butanol (75 ml). The combined organic phases were separated to few portions.
1) $Bu_3N$ (10.4 ml) was added, and the mixture was cooled to 2° C., and stirred for 2 hours. The solid was filtered, washed and dried at 55° C. under vacuum, providing (S)-PREGABALIN with a total purity of 99.7% area by HPLC, CMH-Diacid—0.11% area by HPLC.
2) Water (10 ml) and $Bu_3N$ (10.4 ml) were added. The mixture was cooled to 2° C., and stirred for 2 hours. The solid was filtered, washed, and dried at 55° C. under vacuum, providing (S)-PREGABALIN with a total purity of 99.7% area by HPLC, CMH-Diacid—0.13% area by HPLC.

Example 5

Preparation of (S)-Pregabalin

A reactor (0.1 l) was loaded with water (50 ml) and NaOH (10.8 gr) to obtain a solution. The solution was cooled to 15° C., and (R)-CMH (10 g) was added. $Br_2$ (8.6 g) was added dropwise (15 min) while keeping the temperature below 20° C. The mixture was heated to 60° C. for 15 minutes, and then cooled to room temperature. Iso-butanol (60 ml), followed by a solution of $H_2SO_4$ (66%) (10 ml), was added. The phases were separated, and the aqueous phase was extracted with Iso-butanol (25 ml). To the combined organic phases, $Bu_3N$ (9.9 g) was added, and the mixture was cooled to 2° C., and stirred for 2 hours. The solid was filtered, washed and dried at 55° C. under vacuum, providing (S)-PREGABALIN with a total purity of 99.88% area by HPLC, CMH-Diacid—0.12% area by HPLC.

Example 6

Preparation of (S)-Pregabalin

A reactor (0.5 l) was loaded with water (165 ml) and NaOH (35.5 g) to obtain a solution. The solution was cooled to 15° C., and (R)-CMH (33 g) was added. $Br_2$ (28.51 g) was added dropwise (15 min) while keeping the temperature below 25° C. The mixture was heated to 60° C. for 15 minutes, and then cooled to 15° C. Iso-butanol was added (100 ml) and then a solution of $H_2SO_4$ (66%) (33 ml) was added. The phases were separated, and the aqueous phase was extracted with Iso-butanol (83 ml). To the combined organic phases, $Bu_3N$ (34.2 g) was added, and the mixture was cooled to 2° C., and stirred for 2 hours. The solid was filtered, washed, and dried at 55° C. under vacuum, providing (S)-PREGABALIN with a total purity of 99.86% area by HPLC, CMH-Diacid—0.14% area by HPLC.

Example 7

Crystallization of (S)-Pregabalin

A flask (0.1 l) was loaded with iso-butanol (25 ml), water (10 ml), and (S)-Pregabalin crude (5 g, contains 0.44% CMH-Diacid) to obtain a mixture. The mixture was heated to reflux until dissolution. The solution was cooled to 2° C., and was stirred for 1.5 hours to induce precipitation. The precipitate was filtered, washed, and dried at 55° C. under vacuum, providing (S)-Pregabalin with a total purity of 99.91% area by HPLC, CMH-Diacid—0.09% area by HPLC.

Example 8

Crystallization of (S)-Pregabalin

A flask (0.1 l) was loaded with iso-butanol (25 ml), water (5 ml), and (S)-Pregabalin crude (5 g, contains 0.44% CMH-Diacid) to obtain a mixture. The mixture was heated to reflux and stirred for 10 minutes to obtain a solution. The solution was cooled to 2° C., and was stirred for 1.5 hours to induce precipitation. The precipitate was filtered, washed, and dried at 55° C. under vacuum, providing (S)-Pregabalin with a total purity of 99.85% area by HPLC, CMH-Diacid—0.07% area by HPLC.

Example 9

Crystallization of (S)-Pregabalin

A flask (0.1 l) was loaded with iso-butanol (20 ml), water (10 ml), and (S)-Pregabalin crude (5 g, contains 0.44% CMH-Diacid) to obtain a mixture. The mixture was heated to reflux until dissolution. The solution was cooled to 10° C., and was stirred for 1.5 hours to induce precipitation. The precipitate was filtered, washed, and dried at 55° C. under vacuum, providing (S)-Pregabalin with a total purity of 99.72% area by HPLC, CMH-Diacid—0.1% area by HPLC.

Example 10

Crystallization of (S)-Pregabalin

A flask (0.1 l) was loaded with iso-butanol (20 ml), water (10 ml), and (S)-Pregabalin crude (5 g, contains 0.44% CMH-Diacid) to obtain a mixture. The mixture was heated to reflux until dissolution. The solution was cooled to 2° C., and was stirred for 1.5 hours to induce precipitation. The precipitate was filtered, washed, and dried at 55° C. under vacuum, providing (S)-Pregabalin crude with a total purity of 99.91% area by HPLC, CMH-Diacid—less then 0.03% area by HPLC.

Example 11

Crystallization of (S)-Pregabalin

A flask (0.1 l) was loaded with iso-butanol (16 ml), water (8 ml), and (S)-Pregabalin crude (4 g, contains 0.37% CMH-Diacid) to obtain a mixture. The mixture heated to reflux until dissolution. The solution was cooled to 2° C., and was stirred for 1 hour to induce precipitation. The precipitate was filtered, washed, and dried at 55° C. under vacuum, providing (S)-Pregabalin with a total purity of 99.72% area by HPLC, CMH-Diacid—0.08% area by HPLC.

What is claimed is:

1. A pregabalin composition containing CMH-diacid of the following structure

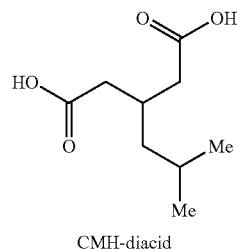

CMH-diacid in an amount from about 0.15% to about 0.03% by HPLC.

2. The Pregabalin composition of claim 1, containing CMH-diacid in an amount from about 0.10% to about 0.03% by HPLC.

3. The Pregabalin composition of claim 1, containing CMH-diacid in an amount from about 0.07% to about 0.03% by HPLC.

4. The Pregabalin composition of any one of claims 2 and 3, wherein the Pregabalin is (S)-Pregabalin of the formula

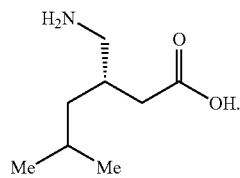

5. A pharmaceutical formulation comprising the (S)-Pregabalin composition of claim 4, and at least one pharmaceutically acceptable excipient.

6. A process for preparing a pharmaceutical formulation comprising mixing the (S)-Pregabalin composition according to claim 4 with a pharmaceutically acceptable carrier to form said pharmaceutical formulation.

* * * * *

UNITED STATES PATENT AND TRADEMARK OFFICE
CERTIFICATE OF CORRECTION

PATENT NO. : 7,462,737 B2  Page 1 of 1
APPLICATION NO. : 11/432090
DATED : December 9, 2008
INVENTOR(S) : Hedvati et al.

It is certified that error appears in the above-identified patent and that said Letters Patent is hereby corrected as shown below:

Column 14
Lines 8-9, change "claims 2 and 3" to --claims 1, 2 and 3--

Signed and Sealed this

Twenty-fifth Day of August, 2009

David J. Kappos
*Director of the United States Patent and Trademark Office*